United States Patent [19]
Saya et al.

[11] Patent Number: 6,022,690
[45] Date of Patent: Feb. 8, 2000

[54] POLYNUCLEOTIDES FOR DETECTING LEISHMANIAS AND METHOD OF DETECTION OF LEISHMANIAL PROTOZOAN

[75] Inventors: Hideyuki Saya; Tatsuyuki Mimori; Jiichiro Sasaki, all of Kumamoto; Motomi Nakata, Yokohama, all of Japan

[73] Assignee: Sumitomo Electric Industries, Ltd., Osaka, Japan

[21] Appl. No.: 08/930,797

[22] PCT Filed: Apr. 2, 1996

[86] PCT No.: PCT/JP96/00893

§ 371 Date: Jan. 7, 1998

§ 102(e) Date: Jan. 7, 1998

[87] PCT Pub. No.: WO96/31623

PCT Pub. Date: Oct. 10, 1996

[30] Foreign Application Priority Data

Apr. 4, 1995 [JP] Japan .................................. 7-079087

[51] Int. Cl.[7] .............................. C12Q 1/68; C12P 19/34; C07H 21/04

[52] U.S. Cl. .......................... 435/6; 435/91.2; 536/24.32; 536/24.33; 536/23.7

[58] Field of Search ..................... 435/6, 91.2; 536/24.3, 536/24.32, 24.33, 23.7

[56] References Cited

FOREIGN PATENT DOCUMENTS

| | | |
|---|---|---|
| 0 420 435 A2 | 4/1991 | European Pat. Off. . |
| WO 84/01174 | 3/1984 | WIPO . |

OTHER PUBLICATIONS

Maarten H.L. et al., Diagnosis of New World Leishmaniasis: Specific Detection of Species of the Leishmania Braziliensis Complex by Amplification of Kinetoplast DNA, Acta Tropica, (1992), vol. 52, 45–58.

Eresh S. et al., Identification and Diagnosis of Leishmania Mexicana Complex Isolates by Polymerase Chain Reaction, Parasitology, (1992), vol. 109, p. 423–433.

Smyth A.J. et al, Rapid and Sensitive Detection of Leishmania Kinetoplast DNA from Spleen and Blood Samples of Kala–Azar Patients, Parasitology, (1992) vol. 105, p. 183–192.

Piarroux R. et al., Isolation and Characterization of a Repetitive DNA Sequence from Leishamania Infantum: Development of a Visceral Leishmaniasis Polymerase Chain Reaction, Am. J. Trop. Med., (1993), vol. 49, p. 364–369.

Ikagaku Daijiten 49, Encyclopedia of Medical Seiences, Published in Apr. 1993, Kodansha (with concise English explanation).

Mimori T. et al., Classification of Leishmania Parasites, using kDNA Finger Printing Method by . . . , Japanese Journal of Parasitololy, Apr. 5–6, 1995.

Kaluza. GenBank Accession No. S72847, Jan. 1993.

Berbee et al. GenBank Accession No. U00977, Aug. 1993.

Weissenbach. Genbank Accession No. Z23401, Nov. 1994.

Kano. GenBank Accession No. D12624, Jan. 1994.

*Primary Examiner*—Carla J. Myers
*Attorney, Agent, or Firm*—Pillsbury Madison & Sutro LLP

[57] ABSTRACT

The present invention enables detection, and isolation of DNP, specific to leishmanias, and identification of the sequence thereof.

Accordingly, a leishmania protozoan can be precisely detected. The present invention can be applied to a diagnosis reagent, diagnosis kit, and the like for diagnosing infection with a leishmania protozoan. Furthermore, brazil type leishmanias and mexico type leishmania can be differentiated, whereby the present invention can be applied to development of a remedy after the diagnosis of the leishmania infection. The present invention can be applied also to development of a reagent, a diagnosis kit, and the like for large-group examination for examining quickly and simply a large number of samples at a time in leishmaniasis propagating area.

8 Claims, 7 Drawing Sheets

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 263 nucleic acids
      (B) TYPE: nucleic acid
      (C) STRANDEDNESS: double
      (D) TOPOLOGY: linear    (ii) MOLECULE TYPE: DNA    (xi) SEQUENCE DESCRIPTION: SEQ ID NO:1:

```
CTGTGTTAAT CTCAGTCGTC CTTCTCTTCT CTTCTGACTG GCTCGGCGCT CGGTACCGCT      60

TCTCGTTTCG CTTTGAACGG GAGAGCGGAG GAGAACGAGG AGGTGGGCGT ATCTGCTGAT     120

GAGAGCGGTC GGATCTGCAT GCATCACCGG TCCCTCGGAT GCACACACAT ACACACACAC     180

TCGGCCCGCA GTCCCTCGCT TTGTGCCGCC TTTTTTCTTG TCTTGCCTTA CGCCATGTAC     240

TGCGACCACC CACACACACA CAC                                             263
```

(2) INFORMATION FOR SEQ ID NO:2:

(i) SEQUENCE CHARACTERISTICS:
      (A) LENGTH: 23 nucleic acids
      (B) TYPE: nucleic acid
      (C) STRANDEDNESS: double
      (D) TOPOLOGY: linear    (ii) MOLECULE TYPE: DNA    (xi) SEQUENCE DESCRIPTION: SEQ ID NO:2:

```
CTGACTGGCT CGGCGCTCGG TAC                                              23
```

(2) INFORMATION FOR SEQ ID NO:3:

(i) SEQUENCE CHARACTERISTICS:
      (A) LENGTH: 22 nucleic acids
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:3:

GGTCGCAGAA CATGGCGTAA GG                                        22

(2) INFORMATION FOR SEQ ID NO:4:

(i) SEQUENCE CHARACTERISTICS:
        (A) LENGTH: 125 nucleic acids
        (B) TYPE: nucleic acid
        (C) STRANDEDNESS: double
        (D) TOPOLOGY: linear     (ii) MOLECULE TYPE: DNA     (xi) SEQUENCE DESCRIPTION: SEQ ID NO:4:

GTTCATGCAC GCCACTACTT GCAAGGGTCA CTCGGCATTT TGCGAGGATA AAGGGAAAGA        60

GTTGACATTG CGGCGGAGGT TAGACATGCA AGTCAGGGCA CGGATGTGCG CCATCTCGTA       120

CCCTG                                                                  125

(2) INFORMATION FOR SEQ ID NO:5:

(i) SEQUENCE CHARACTERISTICS:
        (A) LENGTH: 26 nucleic acids
        (B) TYPE: nucleic acid
        (C) STRANDEDNESS: double
        (D) TOPOLOGY: linear     (ii) MOLECULE TYPE: DNA     (xi) SEQUENCE DESCRIPTION: SEQ ID NO:5:

GTTCATGCAC GCCACTACTT GCAAGG                                    26

(2) INFORMATION FOR SEQ ID NO:6:

(i) SEQUENCE CHARACTERISTICS:
        (A) LENGTH: 24 nucleic acids
        (B) TYPE: nucleic acid
        (C) STRANDEDNESS: double
        (D) TOPOLOGY: linear     (ii) MOLECULE TYPE: DNA     (xi) SEQUENCE DESCRIPTION: SEQ ID NO:6:

CAGGGTACGA GATGGCGCAC ATCC                                      24

(2) INFORMATION FOR SEQ ID NO:7:

(i) SEQUENCE CHARACTERISTICS:
        (A) LENGTH: 30 nucleic acids
        (B) TYPE: nucleic acid
        (C) STRANDEDNESS: double
        (D) TOPOLOGY: linear     (ii) MOLECULE TYPE: DNA     (xi) SEQUENCE DESCRIPTION: SEQ ID NO:7:

ACCGGAATTC TTGGCTGTTG GCACGATGAG                                30

(2) INFORMATION FOR SEQ ID NO:8:

(i) SEQUENCE CHARACTERISTICS:
        (A) LENGTH: 30 nucleic acids
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:8:

TTGCAAGCTT TTATCTGGTT ATATTGACAG                              30

(2) INFORMATION FOR SEQ ID NO:9:

(i) SEQUENCE CHARACTERISTICS:
        (A) LENGTH: 21 nucleic acids
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:9:

AAGTGTTGAT ACCCACTTTG T                                       21

(2) INFORMATION FOR SEQ ID NO:10:

(i) SEQUENCE CHARACTERISTICS:
        (A) LENGTH: 20 nucleic acids
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:10:

CAATGGGTTA CTGTTACAAC                                         20

(2) INFORMATION FOR SEQ ID NO:11:

(i) SEQUENCE CHARACTERISTICS:
        (A) LENGTH: 20 nucleic acids
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:11:

CCTTAGGTTC TGGTAATGAC                                         20

(2) INFORMATION FOR SEQ ID NO:12:

(i) SEQUENCE CHARACTERISTICS:
        (A) LENGTH: 20 nucleic acids
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:12:

GGGTGCAATC TCACTGGGAC                                         20

POLYNUCLEOTIDES FOR DETECTING LEISHMANIAS AND METHOD OF DETECTION OF LEISHMANIAL PROTOZOAN

This application is the national phase of international application PCT/JP96/00893, filed Apr. 2, 1996 which designated the U.S.

TECHNICAL FIELD

The present invention relates to DNA specific to leishmania protozoans, and a method for detecting the leishmania protozoan by use of the DNA.

BACKGROUND ART

Leishmaniasis is a disease caused by infection with a protozoan of Leishmania genus (see, for example, IKA-GAKU DAIJITEN 49, ENCYCLOPEDIA OF MEDICAL SCIENCES, published in April 1993, Kodansha). More than 12,000,000 people are estimated to be suffering from this disease. Leishmaniasis is one of the important diseases designated by WHO. The leishmania protozoans are classified morphologically into two types: amastigote and promastigote. The both types of protozoans are known to promulgate as the promasitgote type when the protozoan is transplanted to an appropriate culture medium.

Three species are known to infect humans: *Leishmania donovani*, *Leishmania tropica*, and *Leishmania braziliensis*.

These three species have not been differentiated from each other morphologically. However, in recent years, these species have come to be known to include subspecies and varieties by immunological and biochemical techniques.

The methods for detection of the pathogen include direct detection of the protozoan, and indirect estimation of infection with the protozoan by immune reaction or a like method.

Of these, the direct detection is sure, but requires long time and complicated operations, being not practicable in a short time and in large numbers.

The known indirect detection methods include Chopra's antimony reaction, Napier's aldehyde reaction, Branchari's euglobulin reaction, and so forth.

Further, complement-fixation reaction, indirect hemagglutination reaction, and indirect immunofluorometry are known as the immunological methods therefor.

The definite identification of the species is conducted by using cultivated protozoan by Adler's test, measurement of buoyant-density of kineplast DNA, isozyme analysis, and so forth as well as the immune reaction.

DISCLOSURE OF INVENTION

As explained above, the known methods of detection of the leishmania protozoan are not practically useful in view of precision, sensitivity, and operation efficiency, and are not applicable to development of a diagnosis medicine and a diagnosis kit for group examination and the like which are potent means for inhibiting the leishmaniasis infection, disadvantageously.

Moreover, although the decisive identification of the species is important for selection or establishment of treatment for the infection, no practically useful identification method is found.

With the above problems, the object of the present invention is to provide a sure and quick method for judging leishmania infection and identifying the species thereof in a large number, and to make possible the development of diagnosis medicines and diagnosis kits for group examination which is effective in inhibiting leishmania infection.

BEST MODE FOR CARRING OUT THE INVENTION

The present invention is described below in detail by reference to the annexed drawings.

The present invention provides methods for detecting and isolating a DNA specific to various leishmanias, for identifying the base sequence thereof, and for judging the leishmania infection and the kind of the leishmania in a test sample.

More specifically, the present invention relates to a polynucleotide containing characteristically, in the molecule, at least the base sequence SEQ ID NO:1:
CTGTGTTAAT CTCAGTCGTC CTTCTCTTCT CTTCT-GACTG GCTCGGCGCT
CGGTACCGCT TCTCGTTTCG CTTTGAACGG GAGAGCGGAG GAGAACGAGG
AGGTGGGCGT ATCIGCTGAT GAGAGCGGTC GGATCTGCAT GCATCACCGG
TCCCTCGGAT GCACACACAT ACACACACAC TCG-GCCCGCA GTCCCTCGCT
TTGTGCCGCC TTTTTTCTTG TCTTGCCTTA CGC-CATGTAC TGCGACCACC
CACACACACA CAC The present invention relates also to a polynucleotide containing characteristically, in the molecule, at least a base sequence capable of hybridizing to the polynucleotide having the above base sequence.

The present invention relates further to a polynucleotide containing characteristically, in the molecule, at least a base sequence capable of hybridizing to the polynucleotide having a base sequence complementary to the above base sequence.

The present invention relates further to a polynucleotide or a complementary polynucleotide comprising a sequence of at least 15 bases selected from the aforementioned three base sequences.

The present: invention relates further to a polynucleotide having a base sequence SEQ ID NO:2 of CTGACTGGCT CGGCGCTCGG TAC.

The present invention relates further to a polynucleotide having a base sequence SEQ ID NO:3 of GGTCGCAGAA CATGGCGTAA GG.

The present invention relates further to a polynucleotide having at least a base sequence SEQ ID NO:4:
GTTCATGCAC GCCACTACTT GCAAGGGTCA CTCG-GCATTT TGCGAGGATA
AAGGGAAAGA GTTGACATTG CGGCGGAGGT TAGACATGCA AGTCAGGGCA
CGGATGTGCG CCATCTCGTA CCCTG The present invention relates further to a polynucleotide containing characteristically, in the molecule, at least a base sequence capable of hybridizing to the polynucleotide having the above base sequence.

The present invention relates further to a polynucleotide containing characteristically, in the molecule, a base sequence capable of hybridizing with the polynucleotide having a base sequence complementary to the above base sequence.

The present: invention relates further to a polynucleotide or a complementary polynucleotide comprising a sequence of at least 15 bases selected from the aforementioned three base sequences.

The present invention relates further to a polynucleotide having a base sequence SEQ ID NO:5 of GTTCATGCAC GCCACTACTT GCAAGG.

The present invention relates further to a polynucleotide having a base sequence of CAGGGTACGA GATGGCG-CAC ATCC.

The present invention relates further to a method of detecting a DNA coming from a leishmania protozoan or a polynucleotide derived from the DNA in a sample by amplifying a DNA coming from a leishmania protozoa by gene amplification reaction with a template of DNA derived from leishmania protozoa contained in a sample and detecting the amplified DNA or a polynucleotide derived from the DNA.

Leishmania Protozoans, Kinds Thereof, and Cultivation Thereof

The seven kinds of leishmania protozoans relates to the present invention:
L. braziliensis panamensis (MHOM/PA/71/LS94)
L. braziliensis braziliensis (MHOM/BR/75/M2904)
L. braziliensis guyanensis (MHOM/BR/75/M4147)
L. mexicana mexicana (MNYC/BZ/62/M379)
L. mexicana aristedesi (MORY/PA/68/GML3)
L. mexicana amazonensis (MHOM/BR/73/M2269)
L. major (MHOM/SU/73/5ASKH)
L. chagasi (MHOM/BR/74/PP75)

Extraction of Gene (DNA)

The method of separation of a DNA from the above protozoan and the method of purification thereof are not specially limited in the present invention, and can be conducted by any known method. In particular, the phenol/chloroform method can be suitably used in the present invention.

Primer for Arbitrarily Primed Polymerase Chain Reaction (AP-PCR Primer)

Gene amplification is conducted for detecting a DNA common to the leishmanias in the present invention. The arbitrary primer therefor is not limited. For example, the present invention uses following six primers selected as arbitrary primers:

INV-1 (5'-ACCGGAATTCTTGGCTGTTGGCACGATGAG-3') SEQ ID NO:7
INV-2 (5'-TTGCAAGCTTTTATCTGGTTATATTGACAG-3') SEQ ID NO:8
LS-3 (5'-AAGTGTTGATACCCACTTTGT-3') SEQ ID NO:9
LS-2 (5'-CAATGGGTTACTGTTACAAC-3') SEQ ID NO:10
MS2-F (5'-CCTTAGGTTCTGGTAATGAC-3') SEQ ID NO:11
MS2-R (5'-GGGTGC,A.TCTCACTGGGAC-3') SEQ ID NO:12

These six primers are useful for detecting only the DNA common to the seven kinds of leishmania protozoans and the DNA specific to the brazil type leishmanias.

Investigation of Gene Amplification Reaction Conditions

The conditions for the gene amplification reaction are not specially limited, and may be established by reference to the method of Saiki, et al. (Saiki, et al., Science, 230, 1350, 1985; Saiki, et al., Science, 239, 487, 1988), and published books (e.g., Molecular cloning, Cold Spring Harbor Laboratory Press, 2nd ed., 1989).

In the present invention, for example, the conditions below are suitably employed.

For the DNA polymerase chain reaction, the conditions below are suitably employed.
(1) one cycle of 94° C. for 5 min,
(2) 10 cycles of 94° C. for 1 min; 37° C. for 1 min; and 72° C. for 1 min,
(3) 30 cycles of 94° C. for 1 min; 60° C. for 1 min; and 72° C. for 7 min,
(4) one cycle of 72° C. for 7 min, and
(5) storage at 15° C.

Detection of Leishmania Protozoan DNA Fragment

The sample after the gene amplification reaction can be separated and analyzed, for example, by a polyacrylamide gel electrophoresis (PAGE) (e.g., Molecular Cloning, Cold Spring Harbor Laboratory Press, 194–196, 1982, 6.36), and the respective bands can be identified, for example, by dying by an ethidium bromide dying method (e.g., Molecular Cloning, Cold Spring Harbor Laboratory Press, 194–196, 1982, 6, Chapter 36).

The DNA common to leishmanias or the DNA specific to a special type leishmania can be selected by comparing the electrophoresis patterns of the amplified DNAs.

Figure 1A:
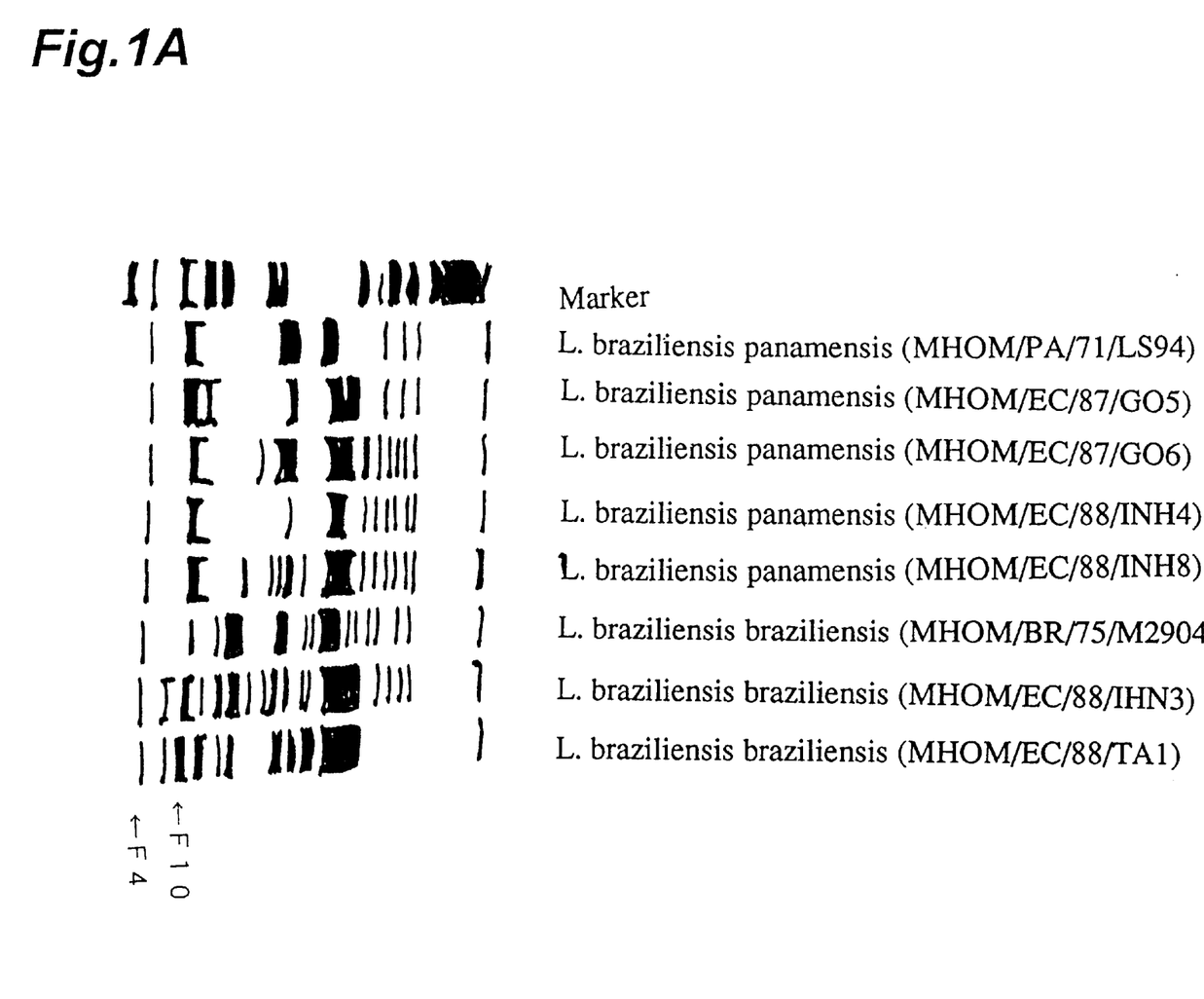
FIG. 1A shows electrophoresis patterns of DNA amplified by a PCR method employing an LS-3 primer.
Figure 1B:
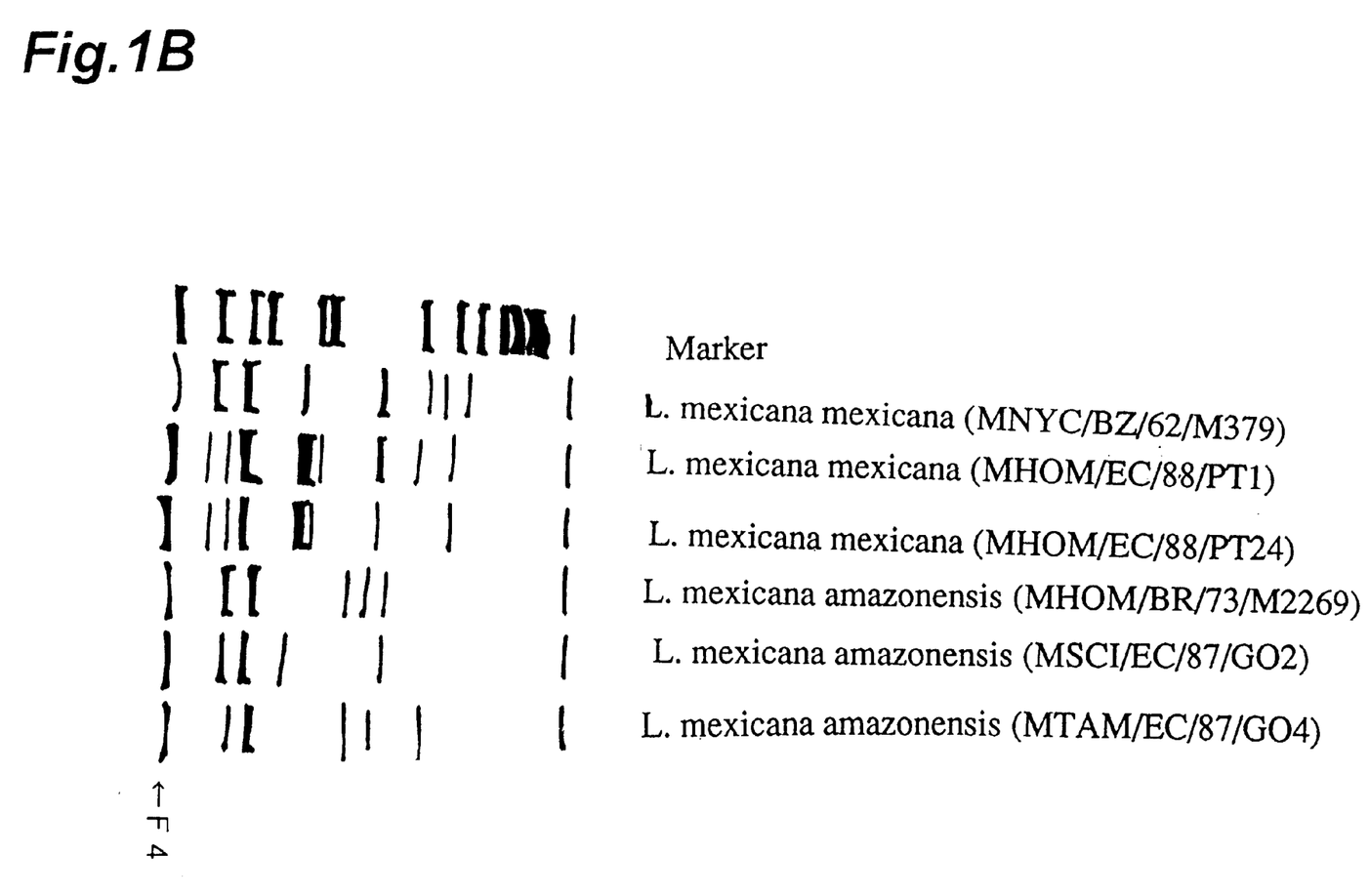
FIG. 1B shows electrophoresis patterns of DNA amplified by a PCR method employing an LS-3 primer.

For example, in the present invention, as shown in FIG. 1A and FIG. 1B, use of the LS-3 primer selected from the above 6 primers enables amplification of a specific band of DNA (referred to as F4) in common to all the leishmanias, and amplification of another specific band of DNA (referred to as F10) in common to the brazil type leishmanias.

Sequencing of Bases of DNAs Specific to Leishmanias

The method of sequencing of the bases of the DNAs of the F4 band and F10 band is not specially limited in the present invention. Known methods including Maxam-Gilbert method, Sanger method, and DNA sequencer method are applicable for the base sequencing. For example, a DNA sequencer, Model 373A manufactured by ABI, is useful. That is, the base sequences of the above two kind of DNAs, F10 and F4, were determined by use of the DNA sequencer of Model 373A produced by ABI, obtaining the base sequence shown in Sequence Tables 1 and 2.

Selection of Polynucleotide for Detection of DNA Specific to Leishmania

The polynucleotide primer (forward primer, and reverse primer) for detecting the DNA specific to leishmania in a sample by gene amplification may be selected from the base sequences of the leishmania-specific DNA as determined above.

For example in the present invention, the polynucleotides having a base sequence shown in SEQ ID NO:5 and 6 may be selected for detection of the DNA band F4.

The polynucleotides having base a sequence shown in SEQ ID NO:2 and 3 may be selected for detection of the DNA band F10.

The preparation method for the selected polynucleotide is not specially limited, and any known oligonucleotide preparation means is applicable. For example, the syn hesis can be conducted generally by use of an automatic DNA synthesis machine, or a like means. In the present invention, the synthesis can be conducted by use of a 392DNA/RNA synthesis machine manufactured by ABI Co.

Furthermore, the leishmania-specific DNA can be amplified by a variety of gene amplification reaction by utilizing the above obtained polynucleotide primer for detection of leishmania-specific DNA.

Gene Amplification Reaction

In the present invention, by adding the detecting polynucleotide of the present invention, namely a primer, to the sample, the leishmania gene can be amplified by a primer elongation reaction if an objective leishmania protozoan is contained in the sample. In the present invention, the method of the gene amplification is not specially limited, and the elongation reaction may be conducted by a general method in which four kinds of nucleotide triphosphate dNTP (deoxyadenosine triphosphate, deoxycytidine triphosphate, cdeoxythymidine triphosphate, and deoxyguanosine triphosphate) as the substrate are bonded to the polynucleotide primer.

The useful enzymes include DNA polymerase I of *Escherichia coli* (*E. coli*), Klenow fragment of *E.coli* DNA polymerase I, T4DNA polymerase, Taq polymerase derived from heat-resistant bacteria, TthDNA polymerase, pfU polymerase, and the like.

In particular, preferred are DNA polymerases derived from heat-resistant bacterias which retain their enzyme activity at a high temperature, since the specificity of the primer to recognize the base sequence of the objective DNA can be raised. (see Japanese Patent Laid-Open Nos. 1-314965 and 1-252300 for the detail).

In the present invention, the DNA of the F10 band common to leishmanias can be amplified efficiently by repeating the elongation reaction by use of combination of the primers shown in SED NO:5 and 6, and the DNA of the F4 band which is specific to brazil type leishmanias can be amplified efficiently by repeating the elongation reaction by use of combination of the primers shown in SEQ ID NO:2 and 3.

The reaction conditions of the gene amplification are selected according to published books, for example: Molecular Cloning 2nd ed., 1989, Cold Spring Harbor Laboratory Press chapter 4; and PCR Jikken Manyuaru, HBJ Shuppann-sha, Jikken Igaku (Experimental Medicine), Special Issue, Vol.8, No.9, 1990, Yodo-sha Co.

Test Samples and Detection Method

The sample to be tested is not limited in the present invention. The DNA band F4 specific commonly to 7 kinds of lehshmanias and the DNA band F10 specific commonly to brazil type leishmanias can be detected by gene amplification with the aforementioned DNA-detecting polynucleotide specific leishmanias.

The test sample can be taken, for example, from the tissue of periphery of a focus judged from its appearance to be infected with leishmania. The sample can be taken, for example, according to the method described in a published book: Byori Hyohon no Tsukurikata (Preparation of Pathology Specimen) (Bunnkodo).

For example, the tissue taken out is enclosed in a compound, quickly frozen by liquid nitrogen or the like, and sliced by a cryostat into frozen section slides, and the obtained section slides can be subjected to gene amplification reaction. In this case, the presence or absence of the gene coming from leishmania can be detected by use of the obtained several slides.

The amplified gene is detectable by a general method. For example, it is separated by agarose electrophoresis, and dyed with ethidium bromide or the like, and the bands of the genes can be detected by ultraviolet light irradiation.

A sample may be a DNA extracted from a taken-out tissue (see, e.g., the method described in Saibo Kogaku Jikken Purotokoru (Experiment Protocol in Cell Engineering) pp.5–7, Shujun-Sha).

That is, the Southern blot technique (Southern, E. M., J.Mol.Biol., 98, 503, 1975) is applied (Molecular Cloning, Cold Spring Harbor Laboratory Press, 2nd ed. 1989).

The DNA derived from the taken-out tissue is treated with a suitable restriction enzyme to obtain fragments thereof, and is separated by electrophoresis. The DNA is transferred onto a membrane like nitrocellulose, and is fixed to the membrane by ultraviolet light irradiation or a like method.

Separately, a portion of the base sequence (preferably sequences of about 36–42 bases) of the F4 band DNA and that of the F10 band DNA are synthesized, and they are labeled for detection. The base sequences are hybridized to the above DNA fixed onto the membrane, whereby the DNA coming from a leishmania can be detected.

The labeling for the detection is conducted with a radioactive isotope such as $^{32}p$ (either at a 3'-terminal or at a 5'-terminal). Also Biotin labeling with an avidin (or streptoavidin)-enzyme complex or hapten labeling with an antibody-enzyme complex are useful for the detection.

Further, the detection can be conducted by dot hybridization (see Saiki, et al., Proc.Natl.Acad.Sci USA, 86, 6230–6234, 1989, or Japanese Patent Laid-Open No. 1-31496). The labeling substance is not specially limited, and fluorescent substances (fluorescein, fluorescein isothiocyanate, rhodamine, tetramethylrhodamine isothiocyanate, Texas Red, phycoerythrin, etc.), and chemiluminescent substances (acridine, Eu-DPTA, etc.) can be used preferably. An indirect method is applicable. Biotin, digoxigenin, and the like are also applicable.

In the present invention, for example, the detection can be conducted by bonding amino-link 2 (produced by ABI Co.) to 5'-terminal of the polynucleotide to be detected.

Judgement of Infection and of Kind of Leishmania Infection

As described above, the F4-band DNA and F10-band DNA can be detected by gene amplification by use of a detecting polynucleotide primer of the present invention. Leishmania infection can be judged by observation of F4, and brazil type leishmania infection can be judged by detection of F10.

EXAMPLE

The present invention is described below in more detail by reference to examples without limiting the invention by the examples.

(1) Extraction of Leishmania Protozoan Gene (Template Gene)

The investigation was conducted with the 7 kinds of protozoans below:

L. braziliensis panamensis (MHOM/PA/71/LS94)
L. braziliensis braziliensis (MHOM/BR/75/M2904)
L. braziliensis guyanensis (MHOM/BR/75/M4147)
L. mexicana mexicana (MNYC/BZ/62/M379)
L. mexicana aristedesi (MORY/PA/68/GML3)
L. mexicana amazonensis (MHOM/BR/73/M2269)
L. major (MHOM/SU/73/5ASKH)
L. chagasi (MHOM/BR/74/PP75)

The promastigotes of the leishmanias were respectively cultivated in a Schneider medium, recovered therefrom, and suspended in an SE buffer solution (0.15M NaCl, 0.1M EDTA (pH8.0)).

To the resulting suspension liquid, sarcosine was added to dissolve the cells, and Proteinase K was added thereto to allow the reaction to proceed at 60° C. for one hour.

After one hour, the reaction mixture was subjected to centrifugation at 4° C. at 16,000 rpm for 90 minutes.

The supernatant was collected, and thereto an equal amount of al phenol-chloroform solution was added to remove protein.

Then a 2.5-fold amount of ethanol was added thereto, and the mixture was left standing at −80° C. for 20 minutes to al ow the DNA to precipitate.

Further, the mixture was subjected to centrifuge at 16,000 rpm for 10 minutes. The precipitate was dissolved in a TE buffer solution (10 mM Tris-HCl (pH8.0), 1 mM EDTP,) to obtain template DNAs.

(2) Primer for Gene Amplification Reaction

The six primfers below were synthesized as the arbitrary primers.

The synthesis was conducted by means of a DNA synthesizer (manufactured by ABI Co.).

INV-1 (5'-ACCGGAATTCTTGGCTGTTGGCACGATGAG-3') SEQ ID NO:7
INV-2 (5'-TTGCAAGCTTTTATCTGGTTATATTGACAG-3') SEQ ID NO:8
LS-3 (5'-AAGTGTTGATACCCACTTTGT-3') SEQ ID NO:9
LS-2 (5'-CAATGGGTTACTGTTACAAC-3') SEQ ID NO:10
MS2-F (5'-CCTTAGGTTCTGGTAATGAC-3') SEQ ID NO:11
MS2-R (5'-GGGTGCAkTCTCACTGGGAC-3') SEQ ID NO:12

(3) Investigation on Conditions of Gene Amplification

To 50 ng of the template DNA prepared in (1), were added 250 ng respectively of the above arbitrary primers, 15.6 µM of dNTP$_{mix}$, and 0.6 unit of Taq polymerase. Further thereto, 10 mM Tris-HCl (pH8.3), 50 mM KCl, 1.5 mM MgCl$_2$, and 0.001% gelatin were added to the final volume of 25 µL, and the gene amplification was conducted.

The conditions of the gene amplification reaction were as shown below.

(i) 94° C., 5 min: 1 cycle
(ii) 94°C., 1 min; 37° C., 1 min; 72° C., 1 min: 10 cycles
(iii) 94° C., 1 min; 60° C., 1 min; 72° C., 1 min: 30 cycles
(iv) 72° C., 7 min: 1 cycle
(v) Storage at 15° C.

After the gene amplification reaction, 5 µL of the reaction mixture was subjected to 6%-polyacrylamide gel electrophoresis to separate the products, and the separated matters were stained by silver staining.

(4) Detection of Leishmania Protozoan Fragment

The results of (3) were studied with the primers of (2) as shown in FIG. 1A and FIG. 1B.

F10 band characteristic to *L.braziliensis*, and F4 band characteristic to both protozoans of *L.brasiliensis* and *L.mexicana* were detected by use of the primer of LS-3.

(5) Sequencing of Base of DNAS of F4-Band and F10-Band

The objective band portions of the polyacrylaminde gel were cut out, and the bands were extracted (e.g., Molecular Cloning, Cold Spring Harbor Laboratory Press, 2nd ed., 1989).

The DNAs of the respective extracted bands were inserted into a vector by means of a TA cloning kit (Invitrogen Co.).

Sequencing of the DNA of the vector was conducted with M13 universal primer and reverse primer by means of DNA Sequencer 373A (manufactured by ABI Co.).

As the results, the base sequences shown in Sequence Table 1 and Sequence Table 4.

F10 band DNA SEQ ID NO:1
CTGTGTTAAT CTCACGTCGTC CTTCTCTTCT CTTCTGACTG GCTCGGCGCT
CGGTACCGCT TCTCGTTTCG CTTTGAACGG GAGAGCGGAG GAGAACGAGG
AGGTGGGCGT ATCTG° CTGAT GAGAGCGGTC GGATCTGCAT GCATCACCGG
TCCCTCGGAT GCACACACAT ACACACACAC TCGGCCCGCA GTCCCTCGCT
TTGTGCCGCC TTTTTTCTTG TCTTGCCTTA CGCCATGTAC TGCGACCACC
CACACACACA CAC F4 band DNA SEQ ID NO:4
GTTCATGCAC GCCACTACTT GCAAGGGTCA CTCGGCATTT TGCGAGGATA
AAGGGAAAGA GTTGACATTG CGGCGGAGGT TAGACATGCA AGTCAGGGCA
CGGATGTGCG CCATCTCGTA CCCTG (6) Synthesis of Detecting Primers From the base sequence obtained in (5), four base sequences, two from F4 band and two from F10 band, were selected (SEQ ID NO:2 and 3, and SEQ ID NO:5 and 6), and were synthesized as the DNA-detecting primers.

The synthesis was conducted with a DNA synthesizer (manufactured by ABI Co.).

(7) Amplification of DNA specific to Leishmania

The gene amplification reaction was conducted on the template DNA obtained in (1) with the F4 band-detecting primers (SEQ ID NO:5 and 6) and the F10 band-detecting primers (SEQ ID NO:2 and 3) synthesized in (6).

The reaction conditions were the same as in (3) except that the primer was changed.

Specificalsy, to 50 ng of the template DNA prepared in (1), were added 250 ng respectively of the above primers (combination of SEQ ID NO:5 and 6, or combination of SEQ ID NO:2 and 3), 15.6 µM of dNTP$_{mix}$, and 0.6 unit of Taq polymerase. Further thereto, 10 mM Tris-HCl (pH8.3), 50 mM KCl, 1.5 mM MgCl$_2$, and 0.001% gelatin to adjust the final volume to 25 µL, and the gene amplification was conducted.

The conditions of the gene amplification reaction were as shown below.
(i) 94° C., 5 min: 1 cycle
(ii) 94° C., 1 min. 60° C., 1 min; 72° C., 7 min: 30 cycles
(iii) 72° C., 7 min: 1 cycle
(iv) Storage at 15° C.

After the gene amplification reaction, 5 μL of the reaction mixture was subjected to 6%-polyacrylamide gel electrophoresis to separate the products, and the separated matters were stained by silver staining.

Figure 2A:
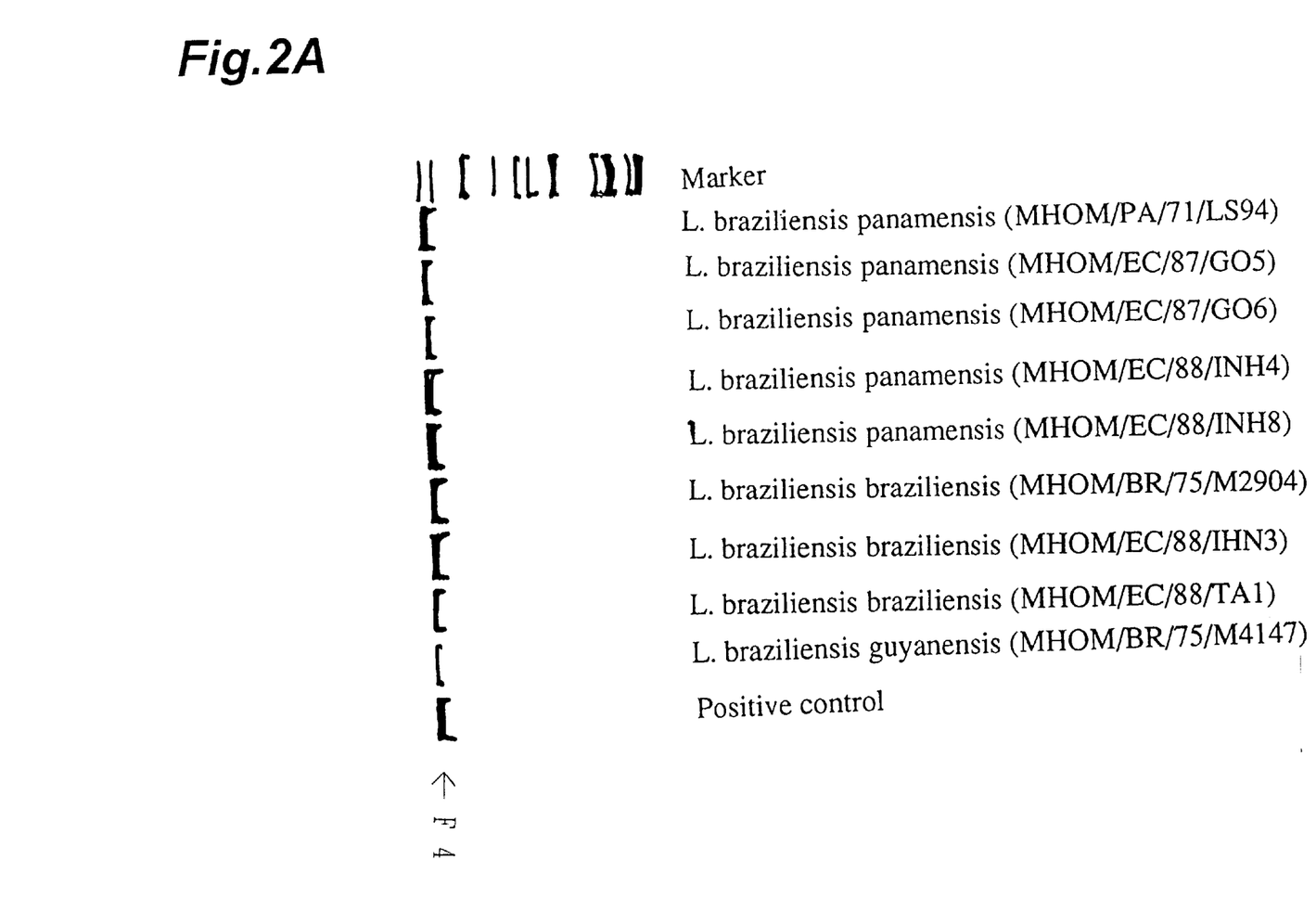
FIG. 2A shows that amplification of DNAs of the F4 band is observed in all kinds of leishmanias when F4 detection primers (SEQ ID NO:5 and 6) are employed.
Figure 2B:
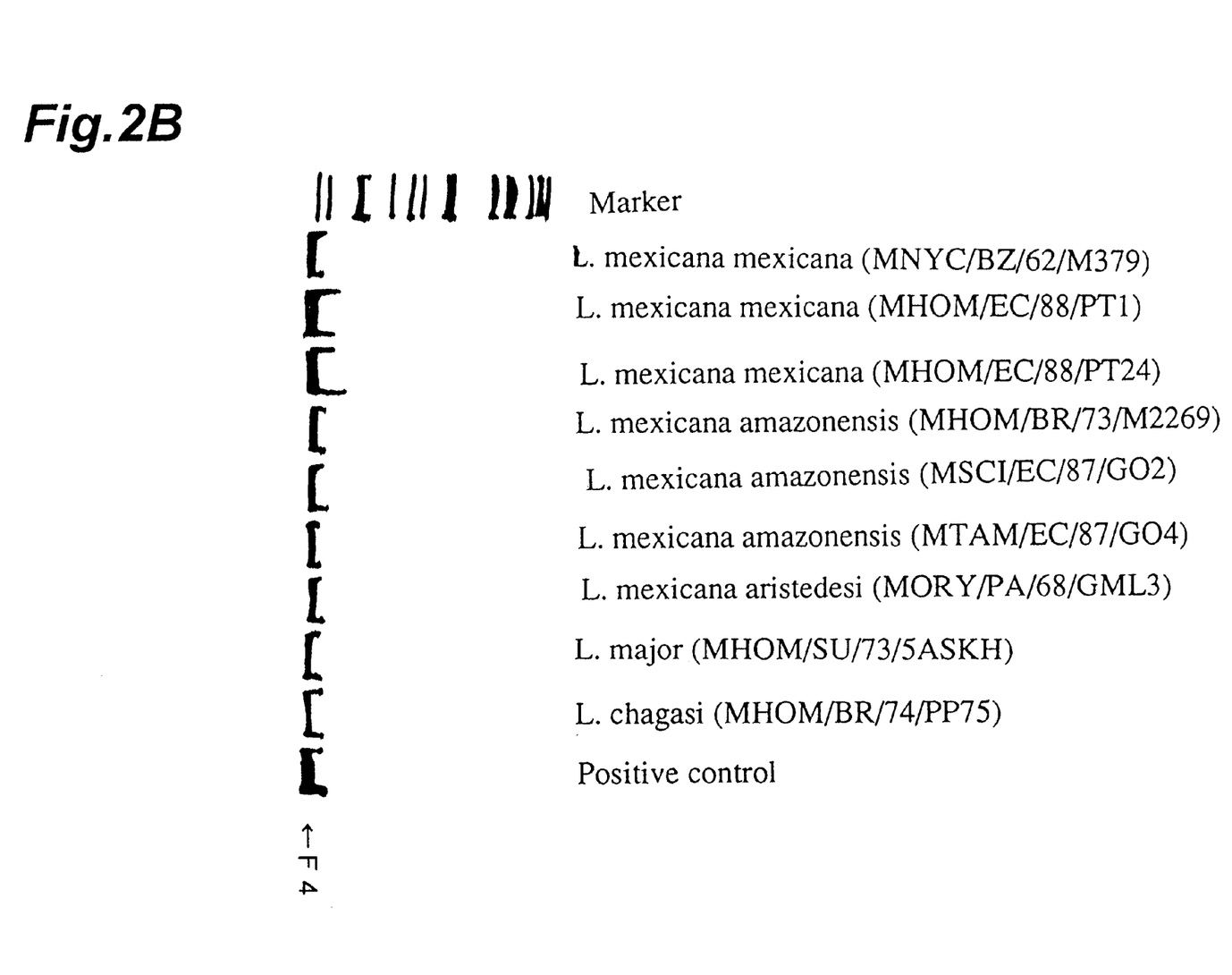
FIG. 2B shows that amplification of DNAS of the F4 band is observed in all kinds of leishmanias when F4 detection primers (SEQ ID NO:5 and 6) are employed.

With the F4-detecting primers (SEQ ID NO:5 and 6), amplification of F4 band DNA was observed in all the kinds of leishmanias (FIG. 2A and FIG. 2B).

Figure 3A:
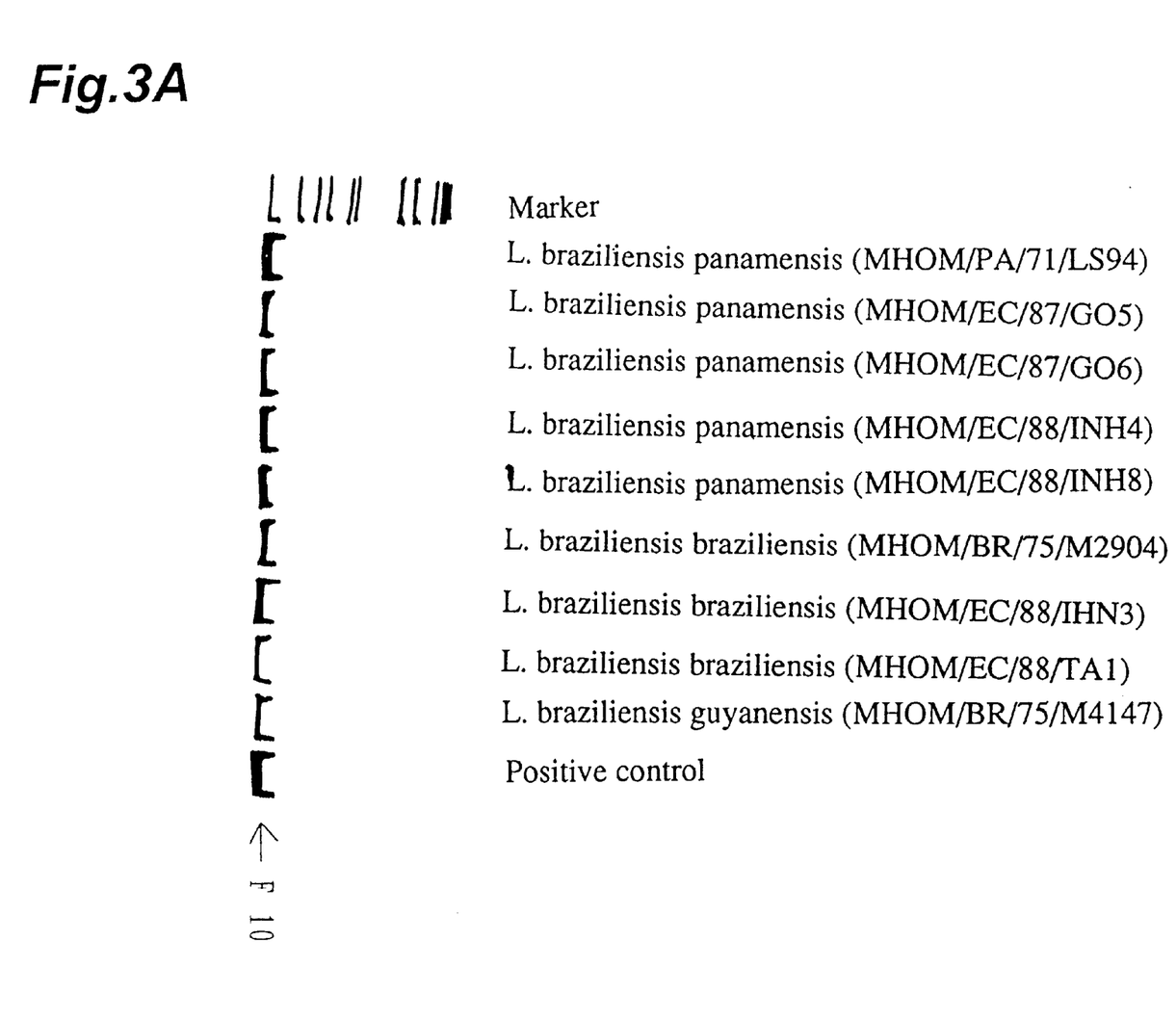
FIG. 3A shows that amplification of DNAs of the F10 band is observed only in *Leishmania braziliensis* type when F10 detection primers (SEQ ID NO:2 and 3) are employed.
Figure 3B:
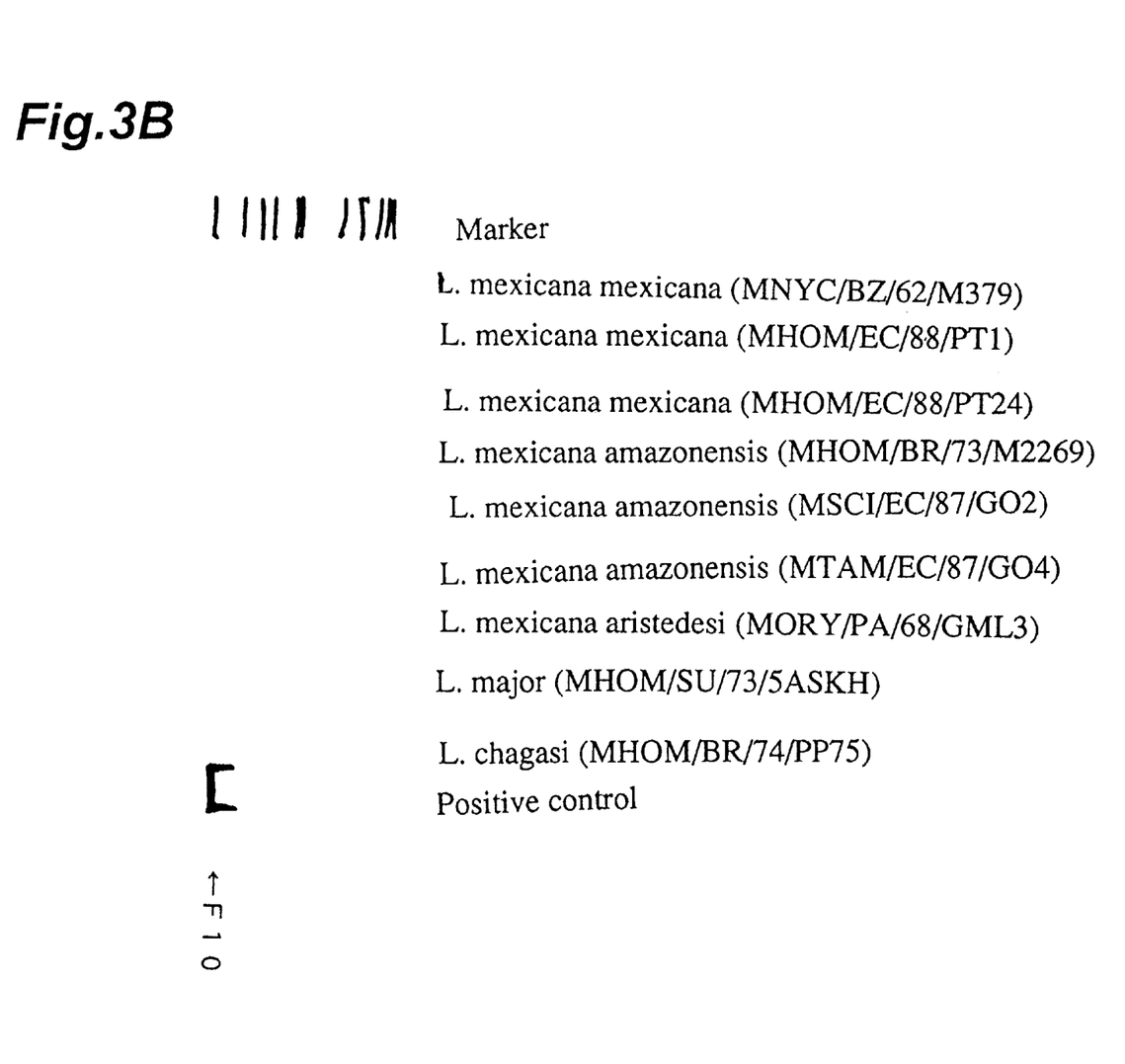
FIG. 3B shows that amplification of DNAs of the F10 band is observed only in *Leishmania braziliensis* type when F10 detection primers (SEQ ID NO:2 and 3) are employed.

With the F10-detecting primers (SEQ ID NO:2 and 3), amplification of F10 band DNA was observed only in brazil type leishmanias (FIG. 3A and FIG. 3B).

Figure 4:
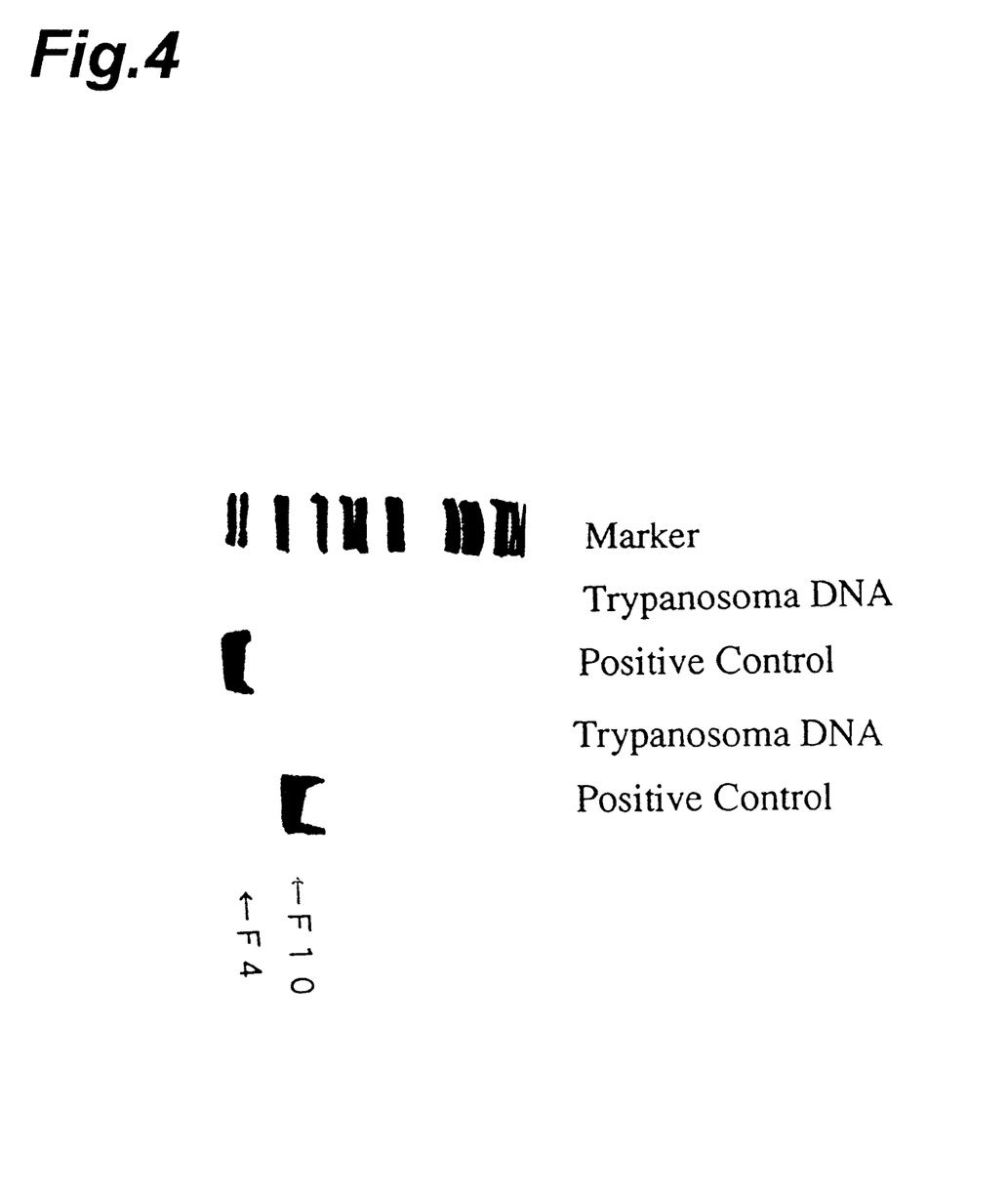
FIG. 4 shows that a trypanosome, a relative parasite, gives no amplified DNA when the F4 detection primers and the F10 detection primers are employed.

Furthermore, with a trypanosoma, a relative parasite, amplification of DNA by F4 band-detecting primer and F10 baind-detecting primer was investigated, and no amplification was caused (FIG. 4). Thus the above amplification was confirmed to be specific to the leishmania protozoans.

INDUSTRIAL APPLICABILITY

The present invention enables detection of DNA specific to leishmanias, isolation thereof, and identification of the base sequence thereof.

Since the leishmania protozoan can be detected precisely in a specimen, the present invention can be applied to a diagnosis reagent, a diagnosis kit, and the like for diagnosing the infection with the leishmania protozoan. Further, since the brazil type and the mexico type of leishmanias can be differentiated, useful judgement data can be obtained for treatment of leishmaniasis after leishmania infection has been confirmed. Furthermore, a reagent, a diagnosis kit, or the like for diagnosis of many specimens quickly and simply at a time for large group diagnosis can be developed according to the present invention, for example, for use in the area where leishmania is epidemic.

We claim:

1. An isolated polynucleotide comprising the sequence of SEQ ID NO:1.

2. An isolated polynucleotide comprising the sequence of SEQ ID NO:2.

3. An isolated polynucleotide comprising the sequence of SEQ ID NO:3.

4. An isolated polynucleotide comprising the sequence of SEQ ID NO:4.

5. A polynucleotide having a base sequence set forth in sequence listing SEQ ID NO:5.

6. A polynucleotide having a base sequence set forth in sequence listing SEQ ID NO:6.

7. A method of detecting leishmania protozoan DNA in a sample comprising:

specifically amplifying sample DNA containing at least the nucleotide sequence of SEQ ID NO: 1 or 4; and detecting the amplified DNA wherein the presence of amplified DNA containing SEQ ID NO: 1 or 4 is indicative of the presence of leishmania protozoan DNA.

8. A method of detecting leishmania protozoan DNA in a sample comprising:

specifically amplifying sample DNA containing at least 15 contiguous nucleotides of SEQ ID NO: 1 or 4; and
detecting the amplified DNA wherein the presence of amplified DNA containing the 15 contiguous nucleotides of SEQ ID NO: 1 or 4 is indicative of the presence of leishmania protozoan DNA.

* * * * *